(12) United States Patent
Achkar et al.

(10) Patent No.: US 10,966,934 B2
(45) Date of Patent: Apr. 6, 2021

(54) PROCESS FOR PRODUCING COATED PARTICLES

(71) Applicant: DSM IP ASSETS B.V., Heerlen (NL)

(72) Inventors: Jihane Achkar, Kaiseraugst (CH); Elger Funda, Kaiseraugst (CH); Loni Schweikert, Kaiseraugst (CH); Kai Urban, Kaiseraugst (CH); Olivia Brigitte Vidoni, Kaiseraugst (CH); Ernst Zedi, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/486,572

(22) PCT Filed: Feb. 16, 2018

(86) PCT No.: PCT/EP2018/053855
§ 371 (c)(1),
(2) Date: Aug. 16, 2019

(87) PCT Pub. No.: WO2018/149952
PCT Pub. Date: Aug. 23, 2018

(65) Prior Publication Data
US 2019/0380971 A1  Dec. 19, 2019

(30) Foreign Application Priority Data
Feb. 20, 2017 (EP) .................... 17156871

(51) Int. Cl.
*A61K 9/50* (2006.01)
*A61K 31/216* (2006.01)
(52) U.S. Cl.
CPC .......... *A61K 9/5089* (2013.01); *A61K 9/5015* (2013.01); *A61K 31/216* (2013.01)

(58) Field of Classification Search
CPC .............................. A61K 9/5089; B01J 2/006
USPC ........................................ 424/489; 427/2.15
See application file for complete search history.

(56) References Cited

U.S. PATENT DOCUMENTS

| 4,828,857 | A | * | 5/1989 | Sharma | .................... | A23G 4/02 |
| | | | | | | 426/285 |
| 5,200,236 | A | * | 4/1993 | Lang | ........................ | C11D 3/39 |
| | | | | | | 252/186.25 |
| 5,230,822 | A | * | 7/1993 | Kamel | ................... | B01J 13/043 |
| | | | | | | 252/186.25 |
| 5,258,132 | A | * | 11/1993 | Kamel | .................. | B01J 13/043 |
| | | | | | | 428/402.24 |
| 5,733,575 | A | * | 3/1998 | Mehra | ................. | A61K 9/2813 |
| | | | | | | 424/480 |

(Continued)

FOREIGN PATENT DOCUMENTS

WO     2010/111347         9/2010
WO     WO-2010111347 A2 *  9/2010  ............. A23P 10/35

OTHER PUBLICATIONS

Achanta et al. "Development of Hot Melt Coating Methods." Drug development and industrial Pharmacy, vol. 23, No. 5 Jan. 1, 1997 pp. 441-449 (Year: 1997).*

(Continued)

*Primary Examiner* — Cachet I Proctor
(74) *Attorney, Agent, or Firm* — Nixon & Vanderhye P.C.

(57) ABSTRACT

The present patent application relates to coated particles. These coated particles show improved properties when used in compressed tablets.

13 Claims, 1 Drawing Sheet

Schematic drawing of a coated particle (cross section)

(56) References Cited

U.S. PATENT DOCUMENTS

| | | | | |
|---|---|---|---|---|
| 5,891,476 | A * | 4/1999 | Reo | A61K 9/0056 424/498 |
| 6,025,315 | A * | 2/2000 | Gorlin | C11D 1/83 510/224 |
| 2002/0192278 | A1* | 12/2002 | van Dijk | A61K 47/36 424/465 |
| 2004/0043070 | A1* | 3/2004 | Ayres | A61K 9/4891 424/471 |
| 2006/0177499 | A1* | 8/2006 | Besse | A61P 3/06 424/464 |
| 2008/0085318 | A1* | 4/2008 | Cherukuri | A61K 31/135 424/493 |

OTHER PUBLICATIONS

International Search Report for PCT/EP2018/053855, dated Apr. 9, 2018, 4 pages.
Written Opinion of the ISA for PCT/EP2018/053855, dated Apr. 9, 2018, 5 pages.
Abdul et al., "A flexible technology for modified-release drugs: Multiple-unit pellet system (MUPS)", Journal of Controlled Release, vol. 147, No. 1, Oct. 1, 2010, pp. 2-16.
Achanta et al., "Development of Hot Melt Coating Methods", Drug Development and Industrial Pharmacy, vol. 23, No. 5, Jan. 1, 1997, pp. 441-449.

* cited by examiner

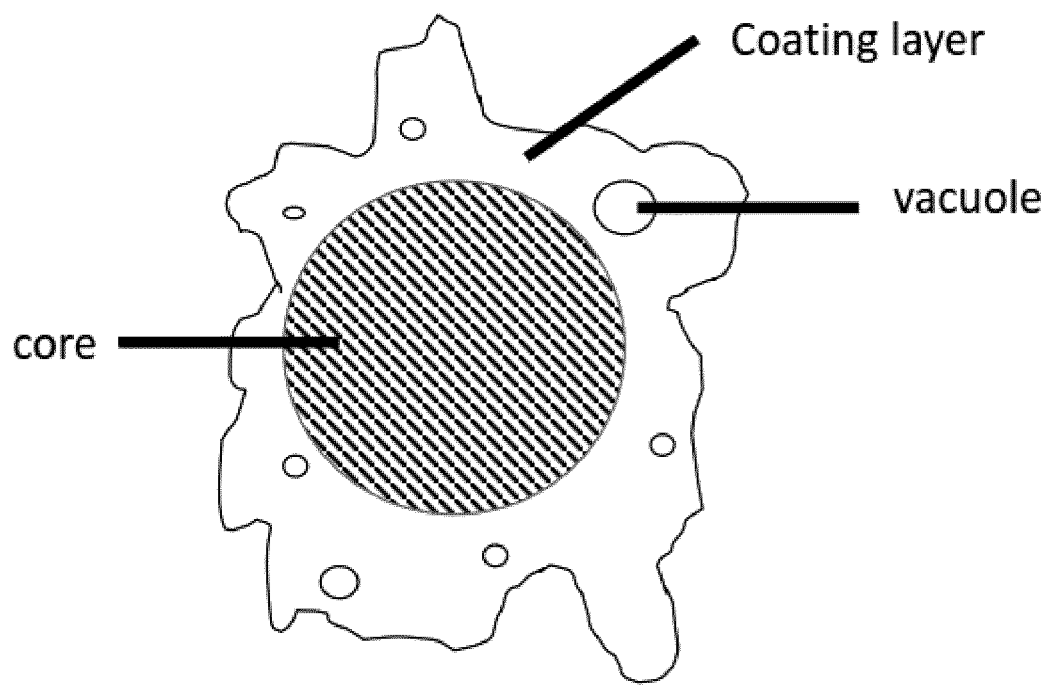
Schematic drawing of a coated particle (cross section)

PROCESS FOR PRODUCING COATED PARTICLES

This application is the U.S. national phase of International Application No. PCT/EP2018/053855 filed 16 Feb. 2018, which designated the U.S. and claims priority to EP Patent Application No. 17156871.0 filed 20 Feb. 2017, the entire contents of each of which are hereby incorporated by reference.

The present patent application relates to a process for producing specific coated particles. These coated particles show improved properties when used in compressed tablets.

Particles which are used to be compacted into tablets usually contain one or more active ingredient, which are essential for the tablet (for need of the consumers). Examples for such active ingredients are vitamins, carotenoids, oils, minerals, plants extract or any other commonly used active ingredient. These active ingredients are first formulated into particles, which are then used for (for example) producing compressed (compacted) tablets or they are used in premixes which are then used for further formulations (such as compressed or compacted tablets).

A major problem and disadvantage in the use of such particles is that when pressure (usually more than 5 kN) is applied on such particles (which comprise the essential ingredients for the tablet), then some of the essential ingredients are usually squeezed out of the particle, degraded within days, and lost for further formulation. Furthermore, a smell issue or a discoloration issue can also arise because of this "squeezing-out"-phenomenon, depending on the active ingredient. This well-known effect is called "initial loss".

To assure that in the final product (for example a compressed or compacted tablet) the correct e.g. desired) amount of the essential ingredient is present, an over dosage of the essential ingredient is usually used nowadays. But over dosage is not an ideal solution of this problem.

It was found that when the specific coated particles are produced by a top spray method, these above-mentioned problems are solved, because the particles have excellent properties.

Therefore, the present invention relates a process (P) for the production of coated particles, wherein the particles comprising
(a) 40 wt-%-95 wt-%, based on the total weight of the coated particle, of a core, comprising at least one active ingredient and
(b) 5 wt-%-60 wt-%, based on the total weight of the coated particle, of a coating system (which forms the coating layer around the core), wherein said coating system comprises at least one wax and/or at least one fat,
characterised in that a top spraying device is used for the coating.

The coated particles, which are obtained, comprise
(a) 40 wt-%-95 wt-%, based on the total weight of the coated particle, of a core, comprising at least one active ingredient and
(b) 5 wt-%-60 wt-%, based on the total weight of the coated particle, of a coating system (which forms the coating layer around the core), wherein said coating system comprises at least one wax and/or at least one fat,
and the particles are characterised in that the coating layer is deformable and irregular in thickness and that said deformable coating layer comprising a plurality of vacuoles.

In such a device (top spray device) the cores (which are to be coated) are introduced into the device (preferably at room temperature and then warmed). Afterwards the molten coating layer compound is sprayed onto the cores.

The inlet temperature is preferably kept at a constant temperature. (preferably around 30-60° C.).

A spraying rate for the molten coating layer compound is also usually kept constant (preferably of 2 g·min$^{-1}$ up to 8 g·min$^{-1}$, more preferably 5 g·min$^{-1}$ up to 6 g·min$^{-1}$). An atomizing air pressure of 1 bar and an atomizing air temperature of 100 to 120° C. were used for the entire process.

The coated particles are cooled down to room temperature into the device and the collected free flowing coated particles are sieved.

Therefore, the present invention also relates to a process (P1), which is process (P), wherein the cores (which are to be coated) are introduced into the device at room temperature.

Therefore, the present invention also relates to a process (P2), which is process (P) or (P1), wherein the inlet temperature kept at a constant temperature.

Therefore, the present invention also relates to a process (P2'), which is process (P2), wherein the inlet temperature kept at a constant temperature of 30-60° C.

Therefore, the present invention also relates to a process (P3), which is process (P), (P1), (P2) or (P2'), wherein the spraying rate for the molten coating layer compound is kept constant.

Therefore, the present invention also relates to a process (P3'), which is process (P3), wherein the spraying rate is 2 g·min$^{-1}$ up to 8 g·min$^{-1}$.

Therefore, the present invention also relates to a process (P3"), which is process (P3), wherein the spraying rate is 5 g·min$^{-1}$ up to 6 g·min$^{-1}$.

Therefore, the present invention also relates to a process (P4), which is process (P), (P1), (P2), (P2)', (P3), (P3') or (P3"), wherein an atomizing air pressure of 1 bar and an atomizing air temperature of 100 to 120° C. is used for the entire process.

The term "coated particle" in the context always refers to a core which is coated by a coating system. Usually the coating covers the whole particle, but it can also have some "defects" where no coating is present (but more than 80% of the surface of the particle is coated).

The term "core" in the context of the present invention always refers to a particle, which is produced by any commonly known and used technology (such as spray drying, spray cooling, spray granulation, spray chilling etc.) and which contains at least one active ingredient.

The coated particles are usually of such a size that tablets can be compacted.

A suitable size of the coated particles is between 50-1000 μm (preferably 100-800 μm); the size is defined by the diameter of the longest dimension of the particle and measured by commonly known method (like light scattering).

All particle sizes of the solid particles according to the present invention are determined by laser diffraction technique using a "Mastersizer 3000" of Malvern Instruments Ltd., UK. Further information on this particle size characterization method can e.g. be found in "Basic principles of particle size analytics", Dr. Alan Rawle, Malvern Instruments Limited, Enigma Business Part, Grovewood Road, Malvern, Worcestershire, WR14 1XZ, UK and the "Manual of Malvern particle size analyzer". Particular reference is made to the user manual number MAN 0096, Issue 1.0, November 1994. If nothing else is stated all particle sizes referring to the coarse particles of the solid particles according to the present invention are Dv90 values (volume diameter, 90% of the population resides below this point, and 10% resides above this point) determined by laser diffraction. The particle size can be determined in the dry form, i.e. as powder or in suspension. Preferably, the particle size of the solid particles according to the present invention is determined as powder.

The distribution of the particle size is also no essential feature of the present invention.

The shape of the core is also not an essential feature of the present invention. The shape can be sphere-like or any other form (also mixtures of shapes). Usually and preferably the cores are sphere-like.

The coating system of the coated particle according to the present invention comprises at least one wax and/or at least one fat.

Waxes in the context of the present invention are organic compounds that characteristically consist of long alkyl chains. Natural waxes (plant, animal) are typically esters of fatty acids and long chain alcohols. Synthetic waxes are long-chain hydrocarbons lacking functional groups.

Fats, which are used for the embodiments of the present invention, consist of a wide group of compounds that are generally soluble in organic solvents and largely insoluble in water. Hydrogenated fats (or saturated fats) in the context of the present invention are generally triesters of glycerol and fatty acids. Fatty acids are chains of carbon and hydrogen atoms, with a carboxylic acid group at one end. Such fats can have natural or synthetic origin. It is possible to hydrogenate a (poly)unsaturated fat to obtain a hydrogenated (saturated) fat.

Especially suitable waxes and fats have a dropping point of from 30 to 85° C., preferably 40 to 70° C.

The dropping point of a material is that temperature (in ° C.) when the material begins to melt under standardized conditions. The material is heated so long until it changes the state of matter from solid to liquid. The dropping point is the temperature when the first dropping is released from the material. The determination of the dropping point (Tropfpunkt) is carried out as described in the standard norm DIN ISO 2176.

Preferred examples of waxes and fats suitable for the present invention are glycerine monostearate, carnauba wax, candelilla wax, soya fat, sugarcane wax, palmitic acid, stearic acid, (fully) hydrogenated cottonseed oil, (fully) hydrogenated palm oil and (fully) hydrogenated rapeseed oil. These compounds can be used as such or as mixtures. Preferred are carnauba wax, candelilla wax, sugarcane wax and (fully) hydrogenated palm oil.

Therefore, the present invention also relates to a process (P5), which is process (P), (P1), (P2), (P2)', (P3), (P3'), (P3") or (P4), wherein the coating system of the coated particles comprises at least one wax and/or at least one fat, which has a dropping point of from 30 to 85° C., preferably 40 to 70° C.

Therefore, the present invention also relates to a process (P6), which is process (P), (P1), (P2), (P2)', (P3), (P3'), (P3"), (P4) or (P5), wherein the coating system of the coated particles comprises at least one wax and/or at least one fat chosen from the group consisting of glycerine monostearate, carnauba wax, candelilla wax, sugarcane wax, palmitic acid, stearic acid, (fully) hydrogenated cottonseed oil, (fully) hydrogenated palm oil and (fully) hydrogenated rapeseed oil.

Therefore, the present invention relates to a process (P6'), which is process (P6), (wherein the coating system of the coated particles comprises at least one wax and/or at least one fat chosen from the group consisting of carnauba wax, candelilla wax, sugarcane wax and (fully) hydrogenated palm oil.

In a preferred embodiment of the present invention the coated particles comprise 50 wt-%-90 wt-%, based on the total weight of the coated particle, of a core and 10 wt-%-50 wt-%, based on the total weight of the coated particle, of a coating system; more preferred 60 wt-%-80 wt-%, based on the total weight of the coated particle, of a core and 20 wt-%-40 wt-%, based on the total weight of the coated particle, of a coating system.

Therefore, the present invention to a process (P7), which is process (P), (P1), (P2), (P2)', (P3), (P3'), (P3"), (P4), (P5), (P6) or (P6'), wherein the coating system of the coated particles comprises 50 wt-%-90 wt-%, based on the total weight of the coated particles, of a core and 10 wt-%-50 wt-%, based on the total weight of the coated particles, of a coating system.

Therefore, the present invention relates to a process (P7'), which is process (P7), wherein the coated particles comprise 60 wt-%-80 wt-%, based on the total weight of the coated particles, of a core and 20 wt-%-40 wt-%, based on the total weight of the coated particles, of a coating system.

The coating system of the coated particles can also comprise further ingredients, which are non-essential for the present invention. Such ingredients can be dyes, flavours, or any other ingredient, which can have a purpose in the compressed tablet.

The core of the coated particles comprises at least one active ingredient, which is needed in the compressed tablet.

The amount in the compressed tablet of the active ingredient(s) can vary and it depends on factors such as for example on the type of active ingredient, on the use of the tablet etc.

The amount of the active ingredient(s) in compressed tablets according to the present invention can be influenced and controlled by the amount of the at least one active ingredient in the core and by the amount of core in relation to coating and finally the amount of the coated particle in the process of production of the compressed tablet.

That active ingredient (or mixture of active ingredients) can be any kind of active ingredient. The ingredients can be oil-soluble or water-soluble.

Suitable ingredients are for example any vitamins, polyunsaturated fatty acids (PUFAs), carotenoids, minerals, plant extracts or any other active ingredient. Suitable ingredients are fat-soluble vitamins, such a vitamin A, D, E, and K (as well as derivatives thereof); water-soluble vitamins such as B-vitamins and vitamin C; and carotenoids such as α-carotene, β-carotene, 8'-apo-β-carotenal, 8'-apo-β-carotenoic acid esters, canthaxanthin, curcumin, astaxanthin, lycopene, lutein, zeaxanthin and crocetin.

Preferred active ingredients in the context of the present invention are fat-soluble vitamins. These are vitamins A, D, E, and K (as well as derivatives of any of these vitamins). Especially preferred is vitamin A and/or its derivatives.

Therefore, the present invention relates to a process (P8), which is process (P), (P1), (P2), (P2)', (P3), (P3'), (P3"), (P4), (P5), (P6), (P6'), (P7) or (P7'), wherein the core of the coated particles comprises at least one active ingredient chosen from the group consisting of vitamins, polyunsaturated fatty acids, carotenoids, minerals, and plant extracts.

Therefore the present invention relates to a process (P8'), which is process (P8), wherein the core of the coated particles comprises at least one active ingredient chosen form the group consisting of fat-soluble vitamins, such a vitamin A, D, E, and K (as well as derivatives thereof); water-soluble vitamins such as B vitamins and vitamin C; and carotenoids such as α-carotene, β-carotene, 8'-apo-β- carotenal, 8'-apo-β-carotenoic acid esters, canthaxanthin, curcumin, astaxanthin, lycopene, lutein, zeaxanthin and crocetin.

Therefore, the present invention relates to a process (P8'''), which is process (P8), wherein the core comprises at least one active ingredient chosen from the group consisting of vitamins A, D, E, and K (as well as derivatives of any of these vitamins).

Therefore, the present invention to a process (P8''''), which is process (P8), wherein the core comprises vitamin A and/or its derivatives.

The amount of the active ingredient in the core of the coated particles, which are used in the process according to the present invention can vary. The amount can be up to 75 wt-%, based on the total weight of the core, of at least one active ingredient. Usually the core comprises at least 0.1 wt-%, based on the total weight of the core, of at least one active ingredient. The content is dependent on the kind of active ingredient (or the mixture of active ingredients) which is used. It could also be higher as well lower.

A very usual range of an amount of the active ingredient in the core is from 0.1-40 wt-%, based on the total weight of the core.

Another very usual range of an amount of the active ingredient in the core is from 0.1-20 wt-%, based on the total weight of the core.

Therefore the present invention relates to a process (P9), which is process (P), (P1), (P2), (P2)', (P3), (P3'), (P3''), (P4), (P5), (P6), (P6'), (P7), (P7'), (P8), (P8'), (P8'') or (P8'''), wherein the amount of the at least one active ingredient in the core of the coated particles is up to 75 wt-%, based on the total weight of the core.

Therefore the present relates to a process (P9'), which is process (P), (P1), (P2), (P2)', (P3), (P3'), (P3''), (P4), (P5), (P6), (P6'), (P7), (P7'), (P8), (P8'), (P8''), (P8''') or (P9), wherein the amount of the at least one active ingredient in the core is at least 0.1 wt-%, based on the total weight of the core.

Therefore the present relates to a process (P9''), which is process (P), (P1), (P2), (P2)', (P3), (P3'), (P3''), (P4), (P5), (P6), (P6'), (P7), (P7'), (P8), (P8'), (P8''), (P8'''), (P9) or (P9'), wherein the amount of the at least one active ingredient in the core of the coated particles is 0.1 wt-%-40 wt-%, based on the total weight of the core.

Therefore the present relates to a process (P9'''), which is process (P), (P1), (P2), (P2)', (P3), (P3'), (P3''), (P4), (P5), (P6), (P6'), (P7), (P7'), (P8), (P8'), (P8''), (P8'''), (P9), (P9') or (P9''), wherein the amount of the at least one active ingredient in the core of the coated particles is 0.1 wt-%-20 wt-%, based on the total weight of the core.

The core of the coated particles used in the process according to the present invention can comprise other components which are used to produce particles (by spray drying, spray cooling, spray chilling, etc), which comprise the active ingredient (s).

The term "core" in the context of the present invention always refers to a particle, which is produced by any commonly known and used technologies (such as spray drying, spray cooling, spray chilling etc.) and which contains at least one active ingredient as defined above.

A preferred core of the coated particle according to the present invention is a core comprising
(i) at least 20 wt-%, based on the total weight of the core, of least one fat soluble vitamin,
(ii) at least one emulsifier, and
(iii) at least one non-reducing sugar.

It also possible to produce and use cores with only these three kinds of ingredients.

Therefore, the present invention relates to a process (P10), which is process (P), (P1), (P2), (P2)', (P3), (P3'), (P3''), (P4), (P5), (P6), (P6'), (P7), (P7'), (P8), (P8'), (P8''), (P8'''), (P9), (P9'), (P9'') or (P9'''), wherein the core comprises
(i) at least 20 weight-% (wt-%), based on the total weight of the solid particles, of least one fat soluble vitamin,
(ii) at least one emulsifier, and
(iii) at least one non-reducing sugar.

Therefore, the present relates to a process (P10'), which is process (P), (P1), (P2), (P2)', (P3), (P3'), (P3''), (P4), (P5), (P6), (P6'), (P7), (P7'), (P8), (P8'), (P8''), (P8'''), (P9), (P9'), (P9'') or (P9'''), wherein the core consists of
(i) at least 20 weight-% (wt-%), based on the total weight of the solid particles, of least one fat soluble vitamin,
(ii) at least one emulsifier, and
(iii) at least one non-reducing sugar.

Preferred non-reducing sugars are non-reducing disaccharides; more preferably sucrose and/or trehalose, most preferred is trehalose.

Sucrose is a disaccharide combination of the monosaccharides glucose and fructose with the formula $C_{12}H_{22}O_{11}$. It is commercially available from many suppliers.

Sucrose is often extracted and refined from either cane or beet sugar for human

Trehalose, also known as mycose or tremalose, is a natural alpha-linked disaccharide formed by an α,α-1,1-glucoside bond between two α-glucose units. There is an industrial process where trehalose is derived from corn starch. There are known biological pathways for trehalose biosynthesis.

Trehalose is available commercially from various suppliers.

The amount of non-reducing sugar in core is from 5-55 weight-% (wt-%), based on the total weight of the core. Preferably 10-50 wt-%, based on the total weight of the core; more preferably 15-45 wt-%, based on the total weight of the core.

Therefore the present invention relates to a process (P11), which is process (P), (P1), (P2), (P2)', (P3), (P3'), (P3''), (P4), (P5), (P6), (P6'), (P7), (P7'), (P8), (P8'), (P8''), (P8'''), (P9), (P9'), (P9''), (P9'''), (P10) or (P10'), wherein the core comprises 5-55 wt-%, based on the total weight of the core, of at least one non-reducing sugar (preferably sucrose and/or trehalose, more preferably trehalose).

Therefore the present invention relates to a process (P12), which is process (P), (P1), (P2), (P2)', (P3), (P3'), (P3''), (P4), (P5), (P6), (P6'), (P7), (P7'), (P8), (P8'), (P8''), (P8'''), (P9), (P9'), (P9''), (P9'''), (P10), (P10') or (P11), wherein the core comprises 10-50 wt-%, based on the total weight of the core, of at least one non-reducing sugar preferably sucrose and/or trehalose, more preferably trehalose).

Therefore the present invention relates to a process (P13), which is process (P), (P1), (P2), (P2)', (P3), (P3'), (P3''), (P4), (P5), (P6), (P6'), (P7), (P7'), (P8), (P8'), (P8''), (P8'''), (P9), (P9'), (P9''), (P9'''), (P10), (P10'), (P11) or (P12), wherein the core comprises 15-45 wt-%, based on the total weight of the core, of at least one non-reducing sugar preferably sucrose and/or trehalose, more preferably trehalose).

Therefore, the present invention relates to a process (P14), which is process (P), (P1), (P2), (P2)', (P3), (P3'), (P3''), (P4), (P5), (P6), (P6'), (P7), (P7'), (P8), (P8'), (P8''), (P8'''), (P9), (P9'), (P9''), (P9'''), (P10), (P10'), (P11), (P12) or (P13), wherein the core comprises 20-75 wt-%, based on the total weight of the core, of the fat-soluble vitamin(s).

Therefore, the present invention relates to a process (P15), which is process (P), (P1), (P2), (P2)', (P3), (P3'), (P3"), (P4), (P5), (P6), (P6'), (P7), (P7'), (P8), (P8'), (P8"), (P8'''), (P9), (P9'), (P9"), (P9'''), (P10), (P10'), (P11), (P12), (P13) or (P14), wherein the core comprises 25-70 wt-%, based on the total weight of the core, of the fat-soluble vitamin(s).

Therefore the present invention relates to a process (P16), which is process (P), (P1), (P2), (P2)', (P3), (P3'), (P3"), (P4), (P5), (P6), (P6'), (P7), (P7'), (P8), (P8'), (P8"), (P8'''), (P9), (P9'), (P9"), (P9'''), (P10), (P10'), (P11), (P12), (P13), (P14) or (P15), wherein the core the at least emulsifier is chosen from the group consisting of modified (food) starches, ascorbyl palmitate, pectin, alginate, carrageenan, furcellaran, dextrin derivatives, celluloses and cellulose derivatives (e.g. cellulose acetate, methyl cellulose, hydroxypropyl methyl cellulose), lignosulfonate, polysaccharide gums (such as gum acacia (=gum arabic), modified gum acacia, TIC gum, flaxseed gum, ghatti gum, tamarind gum and arabinogalactan), gelatine (bovine, fish, pork, poultry), plant proteins (such as are for example peas, soybeans, castor beans, cotton, potatoes, sweet potatoes, manioc, rapeseed, sunflowers, sesame, linseed, safflower, lentils, nuts, wheat, rice, maize, barley, rye, oats, lupin and sorghum), animal proteins including milk or whey proteins, lecithin, polyglycerol ester of fatty acids, monoglycerides of fatty acids, diglycerides of fatty acids, sorbitan ester, and sugar ester (as well as derivatives thereof).

Therefore the present invention relates to a process (P16'), which is process (P), (P1), (P2), (P2)', (P3), (P3'), (P3"), (P4), (P5), (P6), (P6'), (P7), (P7'), (P8), (P8'), (P8"), (P8'''), (P9), (P9'), (P9"), (P9'''), (P10), (P10'), (P11), (P12), (P13), (P14) or (P15), wherein the core the at least emulsifier is not derived from an animal source.

Therefore the present invention relates to a process (P16"), which is process (P), (P1), (P2), (P2)', (P3), (P3'), (P3"), (P4), (P5), (P6), (P6'), (P7), (P7'), (P8), (P8'), (P8"), (P8'''), (P9), (P9'), (P9"), (P9'''), (P10), (P10'), (P11), (P12), (P13), (P14) or (P15), wherein the core the at least emulsifier is chosen from the group consisting of modified (food) starches, polysaccharide gums and plant proteins.

Therefore the present invention relates to a process (P17), which is process (P), (P1), (P2), (P2)', (P3), (P3'), (P3"), (P4), (P5), (P6), (P6'), (P7), (P7'), (P8), (P8'), (P8"), (P8'''), (P9), (P9'), (P9"), (P9'''), (P10), (P10'), (P11), (P12), (P13), (P14), (P15), (P16), (P16') or (P16"), wherein the amount of the emulsifier(s) in the core is 20-70 wt-%, based on the total weight of the core.

Therefore the present invention relates to a process (P17'), which is process (P), (P1), (P2), (P2)', (P3), (P3'), (P3"), (P4), (P5), (P6), (P6'), (P7), (P7'), (P8), (P8'), (P8"), (P8'''), (P9), (P9'), (P9"), (P9'''), (P10), (P10'), (P11), (P12), (P13), (P14), (P15), (P16), (P16') or (P16"), wherein the amount of the emulsifier(s) in core is 25-65 wt-%, based on the total weight of the core.

Therefore, the present invention also relates to a process (P18), which is process (P), (P1), (P2), (P2)', (P3), (P3'), (P3"), (P4), (P5), (P6), (P6'), (P7), (P7'), (P8), (P8'), (P8"), (P8'''), (P9), (P9'), (P9"), (P9'''), (P10), (P10'), (P11), (P12), (P13), (P14), (P15), (P16), (P16'), (P16"), (P17) or (P17'), wherein the core comprises up to 15 wt-%, based on the core, of at least one auxiliary agents.

Therefore, the present invention also relates to a process (P18'), which is process (P18), wherein the auxiliary agent (or auxiliary agents) is chosen from the group consisting of antioxidants (such as ascorbic acid or salts thereof, tocopherol (synthetic or natural)), butylated hydroxytoluene (BHT), ascorbyl palmitate, butylated hydroxyanisole (BHA), propyl gallate, tert. butyl hydroxyquinoline, ethoxyquin and/or ascorbic acid esters of a fatty acid); stabilisers (such as gel-forming agents as xanthan gum, gellan gum); humectants (such as glycerine, sorbitol, polyethylene glycol); dyes; fragrances; fillers and buffers.

All percentages of one coated particle as well as one core always add up to 100%.

An essential feature of the present invention is the irregularity of the coating (coating layer). This means that the coating of the core has not everywhere (all over the core) the same thickness.

The thickness can be 0 (no coating) up to 200 micrometers (μm). Usually the thickness is 0 to 100 micrometers. The thickness can be measured for example using optical or electron microscopy. To get coated particles with the excellent properties as disclosed, the coating layer usually covers at least 80% of the surface of core.

Therefore the present invention also relates to a process (P19), which is process (P), (P1), (P2), (P2)', (P3), (P3'), (P3"), (P4), (P5), (P6), (P6'), (P7), (P7'), (P8), (P8'), (P8"), (P8'''), (P9), (P9'), (P9"), (P9'''), (P10), (P10'), (P11), (P12), (P13), (P14), (P15), (P16), (P16'), (P16"), (P17), (P17'), (P18) or (P18'), wherein the thickness of the coating layer of the obtained coated particle is 0 to 200 μm.

An essential feature of the present invention is that said deformable coating layer comprises a plurality of vacuoles. This usually results in a specific range of roughness.

These vacuoles usually vary in size. They can be from 1 nm to 200 μm. The size is determined by the longest dimension of the vacuole (and it is measured in the same way as the coating layer thickness).

Therefore the present invention also relates to coated particles (CP), which are produced by one of the processes (P), (P1), (P2), (P2)', (P3), (P3'), (P3"), (P4), (P5), (P6), (P6'), (P7), (P7'), (P8), (P8'), (P8"), (P8'''), (P9), (P9'), (P9"), (P9'''), (P10), (P10'), (P11), (P12), (P13), (P14), (P15), (P16), (P16'), (P16"), (P17), (P17'), (P18), (P18') or (P19), wherein the vacuoles of coating layer is from 1 nm to 200 μm.

The coating layer can comprise so many vacuoles that the coating covers still 80% of the core.

As mentioned before the coating particles obtained by any of the processes as described above show less initial loss when compressed (compacted) into tablets. The terms "compressed" and "compacted" (as well as their verbs "compress" and "compact") do mean the same in the context of the present invention.

To produce compress tablets a pressure of 5-40 kN is usually applied.

Therefore the present invention relates to a process (A) for the production of compressed tablets, wherein the coated particles (CP), which are produced by one of the processes (P), (P1), (P2), (P2)', (P3), (P3'), (P3"), (P4), (P5), (P6), (P6'), (P7), (P7'), (P8), (P8'), (P8"), (P8'''), (P9), (P9'), (P9"), (P9'''), (P10), (P10'), (P11), (P12), (P13), (P14), (P15), (P16), (P16'), (P16"), (P17), (P17'), (P18), (P18') or (P19), are compressed with a pressure of a least 5 kN (preferably of 5-40 kN).

The size of the compress tablets can vary and depends on the use of the tablets. Usually they are several millimetres in size. Also, the shape of the compressed tablet can vary (sphere like, egg-like, etc).

The size and the shape of the compressed tablets are not essential features of the present invention.

The compressed tablets could also have an additional coating. This is a non-essential feature.

It also possible to add any additional ingredients, excipients, and/or auxiliary agents to produce the compressed tablets. These are the usual compounds which are used to compress tablets. Such compounds (excipients) are for example, fillers (such as microcrystalline cellulose), acidity regulators (such as calcium phosphate), anti-adherent (such as magnesium stearate), dyes, flavours, sweeteners, etc. The amount of these compounds in the process according to the present invention can vary and depends on the compressed tablets which is produced and the coated particles which are used.

It is also possible to add any kind active ingredients to the tablets as well.

A usual amount of these ingredients is up to 99.9 wt-%, based on the total weight of the compressed tablets.

Therefore the present invention relates to a process (B), which is process (A), wherein 0.1-40 wt-%, based on the total weight of the compressed tablets, of the coated particles (CP), which are produced by one of the processes (P), (P1), (P2), (P2)', (P3), (P3'), (P3"), (P4), (P5), (P6), (P6'), (P7), (P7'), (P8), (P8'), (P8"), (P8'''), (P9), (P9'), (P9"), (P9'''), (P10), (P10'), (P11), (P12), (P13), (P14), (P15), (P16), (P16'), (P16"), (P17), (P17'), (P18), (P18') or (P19), and 60-99.9 wt-%, based on the total weight of the compressed tablets, of at least additional ingredient, excipient and/or auxiliary agent is used.

The percentages add up to 100%.

Therefore, the present invention relates to a process (B'), which is process (B), wherein 0.5-30 wt-%, based on the total weight of the compressed tablets, of the coated particles and 70-99.5 wt-%, based on the total weight of the compressed tablets, of at least additional ingredient, excipient and/or auxiliary agent chosen from the group consisting of fillers (such as microcrystalline cellulose), acidity regulators (such as calcium phosphate), anti-adherent (such as magnesium stearate), dyes, flavours and sweeteners are used.

As stated above the main advantage of the embodiments of the present invention is that the initial loss of the coated particles according to the present invention when compacted (into a tablet) is significantly lower as of the particles of the prior art.

The pressure which is used is to produce tablets is usually between 5 and 40 kN. The tablets can be produce by commonly known and used tablet pressing devices.

Furthermore, the present invention relates to the compress tablets obtained by the process according to the present invention.

The present invention also relates to compressed tablets (CT) comprising
(i) 0.1-40 wt-%, based on the total weight of the compressed tablets, of the coated particles (CP), which comprise 40 wt-%-95 wt-%, based on the total weight of the coated particle, of a core, comprising at least one active ingredient and 5 wt-%-60 wt-%, based on the total weight of the coated particle, of a coating system, and said coating system comprises at least one wax and/or at least one fat,
and
(ii) 60-99.9 wt-%, based on the total weight of the compressed tablets, of at least one additional ingredient, excipient and/or auxiliary agent chosen from the group consisting of fillers (such as microcrystalline cellulose), acidity regulators (such as calcium phosphate), anti-adherent (such as magnesium stearate), dyes, flavours, and sweeteners.

All preferences defined above for the coated particles used in the process according to the present invention also relates to the compressed tablets defined herein.

The present invention also relates to compressed tablets (CT1) comprising
(i) 0.1-40 wt-%, based on the total weight of the compressed tablets, of the coated particles (CP), which comprise 40 wt-%-95 wt-%, based on the total weight of the coated particle, of a core, comprising vitamin A and/or its derivative and 5 wt-%-60 wt-%, based on the total weight of the coated particle, of a coating system consisting of carnauba wax, candelilla wax, sugarcane wax and/or (fully) hydrogenated palm oil,
and
(ii) 60-99.9 wt-%, based on the total weight of the compressed tablets, of at least one additional ingredient, excipient and/or auxiliary agent chosen from the group consisting of fillers (such as microcrystalline cellulose), acidity regulators (such as calcium phosphate), anti-adherent (such as magnesium stearate), dyes, flavours, and sweeteners.

The percentages add up to 100%.

FIGURES

FIG. 1: Schematic drawing of a coated particle (cross section)

The invention is illustrated by the following Examples. All temperatures are given in ° C. and all parts and percentages are related to the weight.

EXAMPLES

Example 1

About 1250 g of particles containing vitamin A acetate having a particle size distribution between 150 μm and 600 μm were coated on a GEA-Niro-AEROMATIC MP1 fluidized bed coating using top spray set up. About 536.0 g of palm oil FH was molten. The cores were introduced into the reactor at room temperature and warmed up at 42° C. The process was then started by spraying the molten palm oil FH on the core with a spraying rate of 5 g·min$^{-1}$ up to 6 g·min$^{-1}$. An atomizing air pressure of 1 bar and an atomizing air temperature of 100 to 120° C. were used for the entire process. The inlet temperature kept constant at 40° C. and the product temperature monitored. The product was cooled down to room temperature into the reactor. The collected free flowing product was sieved to isolate three main fractions.

Total product collected 1640 g.
Yield below 500 μm: 98.6%

| Sieving characteristics | Amount of product [%] |
|---|---|
| <160 μm | <0.1 |
| 160-500 μm | 98.6 |
| >500 μm | 1.4 |
| Total | 100.0 |

The invention claimed is:
1. A process for the production of coated particles having a core and a coating layer surrounding the core, wherein the process comprises the steps of:
(a) forming cores of the coated particles by introducing into a top spraying device 40 wt-% 95 wt-%, based on the total weight of the coated particles, of a core material which consists of:

(i) at least 20 wt-%, based on the total weight of the solid particles, of at least one fat soluble vitamin,
(ii) at least one emulsifier, and
(iii) at least one non-reducing sugar,
(b) introducing into the top spraying device 5 wt-%-60 wt-%, based on the total weight of the coated particles, of a coating system which comprises at least one wax and/or at least one fat selected from the group consisting of carnauba wax, candelilla wax, sugarcane wax and (fully) hydrogenated palm oil, and
(c) operating the top spraying device to spray a molten form of the coating system onto the cores to thereby form the coated particles each comprised of a core formed of the core material and a deformable coating layer having an irregular thickness and a plurality of vacuoles formed of the coating system surrounding the core, wherein
the top spraying device is operated throughout steps (a)-(c) at an atomizing air pressure of 1 bar and an atomizing air temperature of 100 to 120° C.

2. The process according to claim 1, wherein step (a) is practiced by introducing the cores into the top spraying device at room temperature.

3. The process according to claim 1, wherein step (c) includes maintaining an inlet temperature of the top spraying device at a constant temperature.

4. The process according to claim 3, wherein the inlet temperature is maintained at a constant temperature of 30-60° C.

5. The process according to claim 1, wherein the step (c) includes operating the top spraying device so as to maintain a constant spraying rate for the molten form of the coating system.

6. The process according to claim 5, wherein the spraying rate is maintained at a constant spraying rate of 2 g·min$^{-1}$ up to 8 g·min$^{-1}$.

7. The process according to claim 1, wherein the at least one wax and/or at least one fat of the coating system has a dropping point of from 30 to 85° C.

8. The process according to claim 7, wherein the dropping point of the at least one wax and/or at least one fat of the coating system is 40 to 70° C.

9. The process according to claim 1, wherein the coated particles comprise 50 wt-%-90 wt-%, based on the total weight of the coated particles, of the core and 10 wt-%-50 wt-%, based on the total weight of the coated particles, of the coating system.

10. The process according to claim 1, wherein the at least fat soluble vitamin is at least one selected from the group consisting of vitamins A, D, E, and K and derivative thereof.

11. The process according to claim 1, wherein a longest dimension of the vacuoles is from 1 nm to 200 μm.

12. The process according to claim 1, wherein the deformable coating layer covers at least 80% of the core and has a thickness of up to about 200 μm.

13. The process according to claim 12, wherein the thickness of the deformable coating layer is up to 100 μm.

* * * * *